Figure 1:
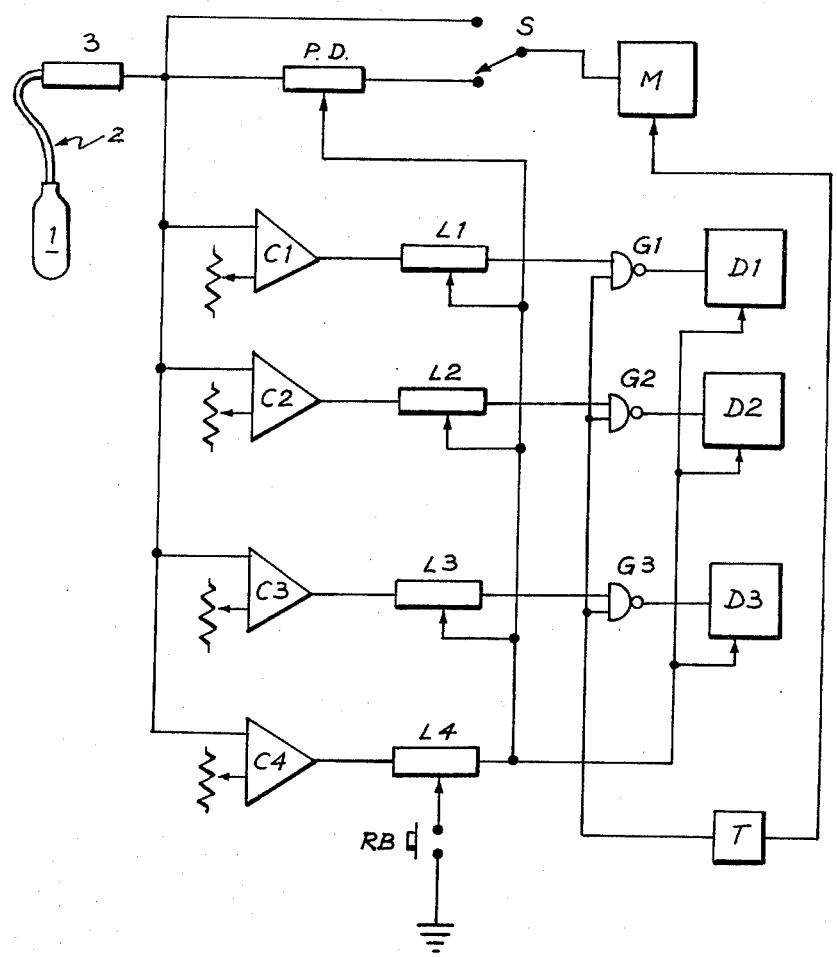

United States Patent [19]

Haski et al.

[11] 4,231,255
[45] Nov. 4, 1980

[54] RATE MEASURING DEVICE FOR JOINT AND/OR MUSCULAR PERFORMANCE

[75] Inventors: André L. Haski, 224 Military Rd., Dover Heights, New South Wales 2030, Australia; Cyriacus A. Bleys, Coogee, Australia

[73] Assignee: said Andre L. Haski, New South Wales, Australia; by said Cyriacus A. Bleys

[21] Appl. No.: 51,670

[22] Filed: Jun. 25, 1979

[30] Foreign Application Priority Data

Jul. 5, 1978 [AU] Australia .............................. PD4951

[51] Int. Cl.³ .............................................. G01L 5/02
[52] U.S. Cl. ...................................... 73/379; 128/774
[58] Field of Search ................................ 73/379–381; 128/774, 26

[56] References Cited

U.S. PATENT DOCUMENTS

| | | | |
|---|---|---|---|
| 2,526,495 | 10/1950 | Meyer | 73/380 |
| 3,420,222 | 1/1969 | Noe et al. | 73/380 |
| 3,690,308 | 9/1972 | Daniels | 128/774 |

*Primary Examiner*—James J. Gill
*Attorney, Agent, or Firm*—Ladas & Parry

[57] ABSTRACT

A device for measuring the rate at which pressure in a bladder is increased by the action of a joint and/or muscle is disclosed. The device permits the time elapsed between predetermined pressure values to be recorded. Preferably the peak pressure reached is also recorded. Such a device finds application in the treatment of patients with rheumatoid arthritis, multiple sclerosis, strokes, head injuries with hemipareses and neuro-muscular diseases.

9 Claims, 2 Drawing Figures

RATE MEASURING DEVICE FOR JOINT AND/OR MUSCULAR PERFORMANCE

The present invention relates to a rate measuring device for measuring joint and/or muscular performance and finds particular application in the diagnosis and treatment of rheumatoid arthritis, multiple sclerosis, strokes, head injuries with hemipareses, and neuromuscular diseases. It is also believed that the present invention will find use in the field of physiotherapy for measuring the progress of a patient under treatment.

It is known to measure the performance of joints and muscles by means of a sealed bladder which contains a fluid, such as air, and which is connected to a pressure transducer. The output of the pressure transducer is then directly connected to an expensive chart recorder which permits a graph of the output voltage, say, of the transducer as a function of time to be recorded.

When the patient squeezes such a bladder the resultant graph shows a rapid increase in pressure above a minimum threshold pressure, the pressure than increases quickly until a maximum pressure is reached at which time the pressure either stabilizes or drops away. From the nature of the curve so obtained, information as to the condition of the patient's joints and muscles can be ascertained and the diagnosis and treatment of the patient is thereby enhanced.

It is the object of the present invention to provide a rate measuring device which is relatively inexpensive compared with the very high cost of the abovedescribed prior art apparatus including a chart recorder. Because of the high cost of such prior art apparatus the number of such pieces of apparatus able to be purchased by a hospital, let alone a medical practitioner in private practice, is extremely limited and therefore the total number of patients able to be treated by such apparatus is also limited.

The present invention comes about because of a realization that the shape of the abovedescribed graph can be easily deduced if only a relatively small number of the points on the graph are known. Therefore it is not necessary to measure the pressure as a function of time but rather it is only necessary to record the pressure at predetermined intervals of time, or, record the time elapsed for predetermined pressures to be achieved.

In accordance with the present invention there is disclosed a rate measuring device for measuring joint and/or muscular performance, said device comprising a sealed bladder containing a fluid and adapted to be squeezed through the action of the joint and/or muscle the performance of which is to be tested; a pressure transducer in fluid communication with said bladder and providing an output indicative of the instantaneous pressure of said fluid; a plurality of comparators each connected to the output of said pressure transducer, the output of each comparator being enabled when said pressure transducer indicates that a corresponding one of a plurality of different predetermined pressure thresholds has been exceeded, the number of said thresholds corresponding to the number of said comparators; and timing and recording means operable by said comparators to record the time at which each pressure threshold is exceeded.

Preferably a peak detector, which is directly connected to the pressure transducer, is also provided so that the peak pressure reached by the fluid in the bladder may be separately recorded by means of a further display device or meter.

Figure 2:
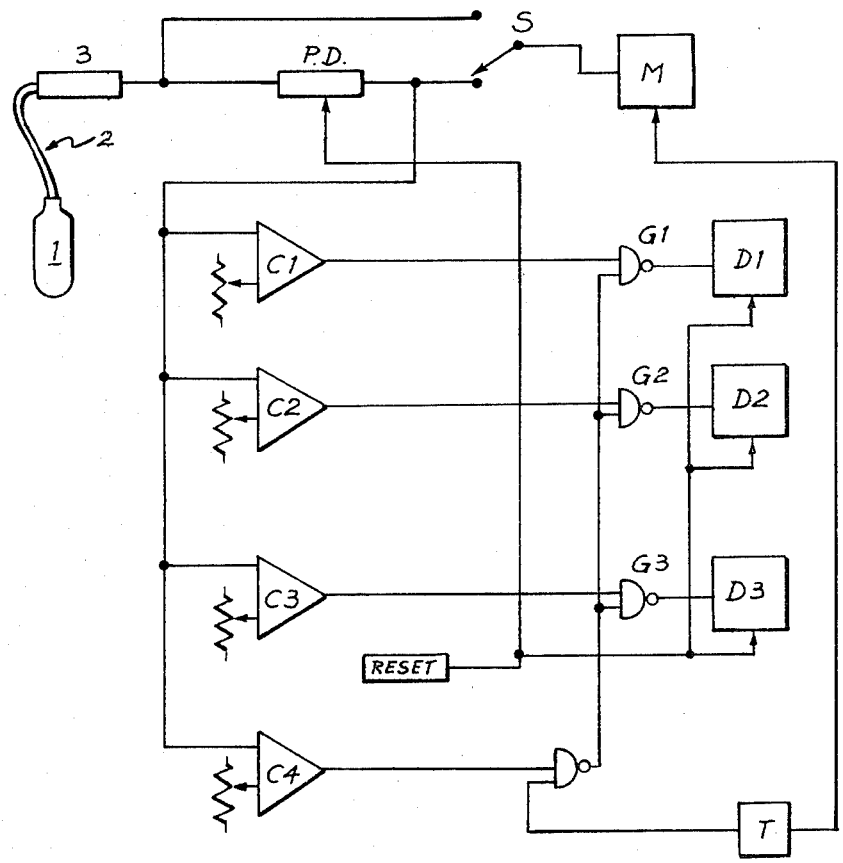

It will be apparent to those skilled in the art of instrumentation and measurement, that the abovedescribed rate measuring device may be realized electrically by means of a pressure to voltage transducer, for example, or may be realized by mechanical means in which the pressure transducer comprises a Bourdon tube, for example. A preferred embodiment of the present invention which realizes the rate measuring device by means of electronic circuitry will now be described with reference to the drawings in which:

FIG. 1 is a schematic block diagram of the electronic rate measuring device of a first embodiment, and FIG. 2 is a schematic block diagram of a second embodiment.

The rate measuring device of the embodiment of FIG. 1 comprises a bladder 1 which is connected by means of a flexible tube 2 to a pressure transducer 3, the output of which is connected to an electronic circuit. The bladder 1 may be formed in any one of a wide variety of shapes and sizes to suit the measurement requirements of particular joints and muscles as well as particular physiological complaints and symptoms. The bladder 1 is sealed and together with the tube 2 provides a predetermined amount of fluid, which is preferably air but could comprise other gases or liquids. The pressure transducer 3 is preferably a commercially available pressure transducer type LX1601G manufactured by National Semiconductor.

The output from the pressure transducer 3 passes directly to a resettable peak detector PD and thence via switch S to a meter M which in the preferred embodiment is a digital display meter but can be a simple moving coil ammeter or voltmeter. The switch S can be operated so as to bypass the peak detector PD and thereby provide an instantaneous direct reading of the output of the pressure transducer 3.

Four comparators C1 to C4 inclusive each have one input connected directly to the output of the pressure transducer 3. The other input of each comparator C1 to C4 is connected to the wiper arm of a corresponding potentiometer. Thus an adjustable presettable voltage, which enables the threshold voltage (at which each comparator responds) to be predetermined, is applied to the other input of each comparator. The output of each comparator C1 to C4 is directly connected to a resettable latch L1 to L4 inclusive. The output of latch L1 to L3 passes via one input of NAND gates G1 to G3 respectively to a resettable digital count display device D1 to D3 respectively.

A timing device T which basically comprises a pulse generator has its outputs connected to the other input of each of the NAND gates G1 to G3 and connected to the digital display meter M respectively. A reset button RB is provided to permit latch L4 to be manually reset and the output of latch L4 is used to reset the peak detector PD, latches L1 to L3, and display devices D1 to D3.

The operation of the circuit of FIG. 1 is as follows. The threshold of comparator C4 is set such that the output of comparator C4 changes state when the output of pressure transducer 3 corresponds to a minimum pressure threshold in the fluid contained in bladder 1, which minimum pressure is achieved substantially immediately after the patient begins to squeeze the bladder 1. Therefore this minimum pressure threshold corresponds substantially to zero time and indicates the beginning of the timing sequence.

Comparators C1 to C3 respectively have their threshold values set so that the output of these comparators changes state when three separate, predetermined pressure levels are achieved. From the time elapsed between the beginning of the squeezing action and the achievement of these predetermined pressure levels, the abovementioned prior art graph of pressure as a function of time may be substantially deduced.

Immediately after the commencement of squeezing of the bladder 1, the comparator C4 changes state as the minimum pressure threshold is exceeded. The change of state of comparator C4 triggers latch L4 thereby immediately resetting the peak detector PD, latches L1 to L3, and display devices D1 to D3. Reset latches L1 to L3 enable NAND gates G1 to G3 so that the pulses received by these gates from the timer T are transmitted directly to each of the display devices D1 to D3 inclusive.

As the pressure of the fluid inside the bladder 1 increases with time, the thresholds of comparators C1 to C3 are sequentially exceeded. Therefore at different times the output of each of the comparators C1 to C3 will change state. When this change of state occurs, the corresponding one of latches L1 to L3 is triggered, thereby inhibiting the corresponding NAND gates G1 to G3 and preventing further pulses from the timer T being recorded at the corresponding display device D1 to D3.

Accordingly the count displayed on each of the display devices D1 to D3 represents the number of pulses which have reached that device and hence the time elapsed between the occurrence of the minimum pressure threshold and the predetermined pressure threshold of the corresponding comparator.

Simultaneously with the above described operation the peak detector PD receives the output from the pressure transducer 3 and applies an ever increasing voltage (or current) to the meter M until such time as the peak voltage produced by the pressure transducer 3 is achieved. As the output of the pressure transducer 3 then begins to fall away, the output of the peak detector PD remains constant thereby ensuring that the meter M provides a reading of the peak pressure reached by the fluid in the bladder 1. This measure is desirable because it indicates the maximum strength of a patient's hand grip, for example, and therefore represents a convenient and reproducable measure for determining whether a particular course of treatment is proving successful.

It will be apparent that the results displayed on the meter M and each of the display devices D1 to D3 may be recorded permanently after the actual squeezing of the bladder since these results will be retained until the next squeezing of the bladder 1 or until the reset button RB is operated thereby resetting the latch L4.

In the embodiment of FIG. 1 the latches L1 to L4 are realized by two NAND gates which are cross-coupled so that the output of each gate provides one of the inputs of the other gate. The remaining input of one of the NAND gates then provides the reset input whilst the remaining input of the other NAND gate receives the change of state of the output of the corresponding comparator. The output of the latches L1 to L4 comprises the output of one of the NAND gates.

The peak detector PD preferably comprises two operational amplifiers, the output of the first amplifier being connected via a diode to the non-inverting input of the second amplifier. The output of the second amplifier is directly connected to both inverting inputs of the amplifiers. Two capacitors are provided, one being connected between the non-inverting input of each amplifier and ground. The capacitor so connected to the non-inverting input of the first amplifier is charged by the output of the pressure transducer 3. It will be seen that the peak detecting function is achieved by the tendency of both operational amplifiers, when so connected, to minimize the difference between their input voltages.

Turning now to FIG. 2, in a second embodiment the outputs of comparators C1 to C3 are directly connected to respective inputs of NAND gates G1 to G3. Furthermore, the output of comparator C4 is connected to one input of NAND gate G4 whilst one output of the timer T is connected to the other input of NAND gate G4.

In addition, comparators C1 to C4 are connected as before, save that all comparators are now connected to the output of the peak detector PD rather than the output of the pressure transducer 3 as in FIG. 1.

In consequence, as soon as the minimum pressure threshold is (immediately) exceeded NAND gate G4 is enabled thereby permitting timing pulses from timer T to be passed to the other inputs of NAND gates G1 to G3. Therefore as soon as each of comparators C1 to C3 is triggered, the corresponding NAND gate is enabled thereby permitting the corresponding display device to receive pulses from timer T.

In this way time lapsed from the minimum pressure threshold to each of the predetermined pressure thresholds is recorded. However, because the output of peak detector P.D. does not fall when the output of pressure transducer 3 falls at the end of each test when the bladder 1 is released, the output of each of the comparators C1 to C4 remains constant.

A reset device, such as reset button RB of FIG. 1, is provided to reset the display devices D1 to D3 and the peak detector P.D. at the end of each measurement. Resetting the peak detector P.D. changes the output of each of the comparators C1 to C4.

The foregoing describes only one embodiment of the present invention and modifications, obvious to those skilled in the art, may be made thereto without departing from the scope of the present invention.

For example, the display devices D1 to D3 comprise integrated circuits type 74C925 manufactured by National Semiconductor, however other types of display devices could be used.

In a further modification, a chart recorder of the prior art type can be directly connected to the input of the meter M in order to provide a conclusive check on the elapsed time indicated in display devices D1 to D3. Either a battery operated or a mains operated device can also be constructed. In the former case the timer T can be a quartz crystal oscillator the output of which is divided to produce the desired pulse rate. In the mains operated device, the mains frequency can be used as the frequency source for the timing pulses.

What we claim is:

1. A rate measuring device for measuring joint and-/or muscular performance, said device comprising a sealed bladder containing a fluid and adapted to be squeezed through the action of the joint and/or muscle the performance of which is to be tested; a pressure transducer in fluid communication with said bladder and providing an output indicative of the instantaneous pressure of said fluid; a plurality of comparators each connected to the output of said pressure transducer, the output of each comparator being enabled when said pressure transducer indicates that a corresponding one of a plurality of different predetermined pressure thresholds has been exceeded, the number of said thresholds corresponding to the number of said comparators; and timing and recording means operable by said comparators to record the time at which each pressure threshold is exceeded.

2. A device as claimed in claim 1 wherein said timing and recording means comprises a pulse generator and a plurality of resettable digital display devices for recording the number of pulses received from said pulse generator.

3. A device as claimed in claim 2 wherein one of said comparators is enabled by a minimum predetermined pressure threshold.

4. A device as claimed in claim 3 wherein the output of each said comparator is directly connected to a corresponding resettable latch device, the output of the one latch device connected to said one comparator being connected to said resettable digital display devices and to the remainder of said resettable latch devices to reset same when said minimum pressure threshold is exceeded, the output of each said remaining latch device being connected to one input terminal of a corresponding logic gate, the pulse generator being connected to the other input terminal of all said logic gates, and the output of each said logic gate being connected to a corresponding one of said display devices whereby pulses from said pulse generator are counted by each reset display device after said minimum pressure threshold has been exceeded and until the pressure threshold of the corresponding comparator has been exceeded, the number of such pulses counted being indicative of the time elapsed therebetween.

5. A device as claimed in claim 4 wherein a peak detector is also connected to the output of said pressure transducer, and a meter is connected to said peak detector to record the peak pressure indicated by said pressure transducer.

6. A device as claimed in claim 4 wherein said latch devices each comprise two cross-coupled NAND gates.

7. A device as claimed in claim 3 wherein a peak detector is directly connected to said pressure transducer, said comparators being connected to said pressure transducer via the output of said peak detector, the output of each comparator being connected to one input of a corresponding logic gate, the output of the one logic gate connected to said one comparator being connected to the other input of the remaining logic gates, the output of each of said remaining logic gates being connected to a corresponding one of said digitial display devices and said pulse generator being connected to the other input of said one logic gate, whereby when said minimum pressure threshold is exceeded said one comparator enables said one logic gate permitting pulses from said pulse generator to be passed via respective ones of said remaining logic gates to said display devices until each of said remaining logic gates is disabled by the corresponding comparator pressure threshold being exceeded, the number of such pulses counted by each display device being indicative of the time elapsed between the exceeding of said minimum pressure threshold and the exceeding of the pressure threshold of the corresponding comparator.

8. A device as claimed in claim 7 including means to reset said peak detector and said display devices.

9. A device as claimed in claim 7 wherein a meter is connected to said peak detector to record the peak pressure indicated by said pressure transducer.

* * * * *